United States Patent
Daifuku et al.

(10) Patent No.: US 8,729,285 B2
(45) Date of Patent: *May 20, 2014

(54) COPPER COMPLEX COMPOUND AND ELECTROPHOTOGRAPHIC TONER CONTAINING THE SAME

(75) Inventors: Koji Daifuku, Tokyo (JP); Ryohei Iwamoto, Tokyo (JP); Keiko Ishidai, Tokyo (JP); Kimihiko Ookubo, Tokyo (JP); Kaori Ono, Tokyo (JP); Issei Nakahara, Tokyo (JP)

(73) Assignee: Konica Minolta Business Technologies, Inc., Tokyo (JP)

( * ) Notice: Subject to any disclaimer, the term of this patent is extended or adjusted under 35 U.S.C. 154(b) by 369 days.

This patent is subject to a terminal disclaimer.

(21) Appl. No.: 13/040,164

(22) Filed: Mar. 3, 2011

(65) Prior Publication Data

US 2011/0152556 A1    Jun. 23, 2011

Related U.S. Application Data

(62) Division of application No. 12/401,934, filed on Mar. 11, 2009, now Pat. No. 7,943,279.

(30) Foreign Application Priority Data

Mar. 14, 2008    (JP) ................. 2008-065483

(51) Int. Cl.
    *C07F 1/00*        (2006.01)
(52) U.S. Cl.
    USPC ........... 556/117; 556/110; 556/113; 556/114; 556/116
(58) Field of Classification Search
    None
    See application file for complete search history.

(56) References Cited

U.S. PATENT DOCUMENTS

| | | |
|---|---|---|
| 2,297,691 A | 10/1942 | Carlson |
| 2007/0092819 A1 | 4/2007 | Daifuku |

FOREIGN PATENT DOCUMENTS

| | | |
|---|---|---|
| JP | 4223910 | 11/1942 |
| JP | 05011504 | 1/1993 |
| JP | 11160914 | 6/1999 |
| JP | 20070316591 | 12/2001 |
| JP | 3567403 | 9/2004 |
| JP | 2007-034254 | 2/2007 |
| JP | 2007034254 | 2/2007 |
| JP | 2007-140478 | 6/2007 |
| JP | 2007-031591 | 12/2007 |
| JP | 2007-316591 | 12/2007 |
| JP | 2009-0036811 | 2/2009 |
| JP | 20090036811 | 2/2009 |
| JP | 2009-217254 | 9/2009 |
| JP | 5109739 | 10/2012 |
| WO | 2008-023657 | 2/2008 |
| WO | 2008023657 | 2/2008 |

OTHER PUBLICATIONS

Japanese Office Action P2008-065483—Nov. 8, 2012.
English language Abstract of Japanese Office Action P2008-065483—Nov. 8, 2012.

*Primary Examiner* — Sudhakar Katakam
(74) *Attorney, Agent, or Firm* — Lucas & Mercanti, LLP

(57) ABSTRACT

A copper complex compound represented by Formula (1) is disclosed.

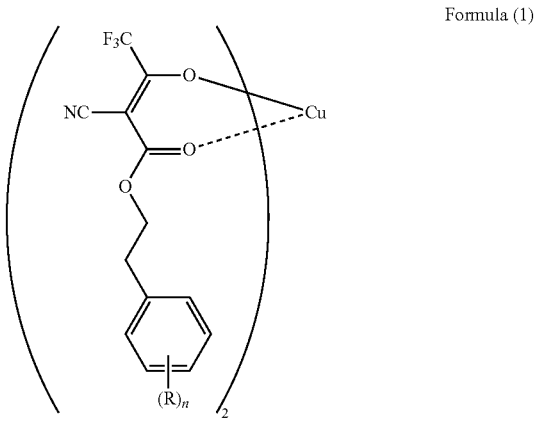

Formula (1)

in the formula, groups represented by R is a substituent, n is an integer of from 1 to 5 and the total carbon number contained in $(R)_n$ is 14 or more. A toner for electrophotography containing the compound is also disclosed.

5 Claims, 1 Drawing Sheet

COPPER COMPLEX COMPOUND AND ELECTROPHOTOGRAPHIC TONER CONTAINING THE SAME

CROSS REFERENCE TO RELATED APPLICATIONS

This is a Divisional Application of U.S. Ser. No. 12/401,934 filed on Mar. 11, 2009 which, in turn, is based on Japanese Patent Application No. 2008-65483 filed on Mar. 14, 2008, the entire content of both Applications is hereby incorporated by reference.

TECHNICAL FIELD

The present invention relates to a copper complex compound and an electrophotographic toner containing the copper compound.

TECHNICAL BACKGROUND OF THE INVENTION

Recently, new image forming means such as color electrophotography, ink-jet ink and color filter are proposed and organic dyes becomes to be used in various fields.

As properties required to the dyes to be used for color image formation, suitable light absorbing property with sharp absorption, low sub-absorption and high light absorption coefficient from the viewpoint of color reproduction, high stability against heat and light, and solubility in a solvent according to the use are cited. It is present situation that sufficient dye is not found out yet though various developments have been carried out for satisfying such the requirements.

As disclosed in various documents, cf. Patent Documents 1 and 2 for example, the electrophotographic method is a method in which an electrostatic latent image is formed by various methods on a photoreceptor containing a photoconductive substance and the latent image is developed by a toner to form a powder image and the powder image is transferred onto paper according to necessity and then fixed by heating, pressing or solvent vapor.

Recently, a color copying method is made practicable, in which an electrostatic latent image of the original is formed by exposing by spectrally separated light and developed by a colored toner to form a colored image and the images different in the color from each other are overlapped to obtain a full color image. As the toner to be used in such the method, toners each colored in yellow, magenta or cyan are produced which are each constituted by a binder and a pigment of and/or dye of each of the colors dispersed in the binder.

By the electrophotographic method, an image is generally formed by the following processes.

Firstly, an electrostatic latent image is formed on a photoreceptor by irradiating light information corresponding to the image information onto the photoreceptor constituted by a photoconductive substance by various methods. After that, the electrostatic latent image formed on the photoreceptor is developed into a toner image by an electrically charged toner, and the toner image is transferred onto an image recording medium such as ordinary paper or an intermediate transferring member and fixed onto the paper using a thermal fixing device.

In the above color image forming method using the electrophotographic system, the electrostatic images formed on the photoreceptor is corresponding to information of images each separated in the colors of yellow, magenta, cyan and black, respectively, and developed by the toner having the color the same as that of the image information. The color image is formed by repeating for four times such the developing for each of the colors.

Hitherto, organic pigments and dyes are used as the colorant to be used for the electrophotographic toner but they each has various drawbacks. For instance, the organic pigments are generally superior to the dye in the heat resistivity and light fastness but the pigments have high covering power and the transparency of them is lowered since they are in a dispersed state. Moreover, the transparency is spoiled and chromaticness is lowered so that the color reproduction of the image is degraded since the dispersibility of the pigment is generally insufficient.

High transparency of the fixed toner is necessary for making possible to observe the color of the toner of the lowest layer without covering by the upper layer and the dispersibility and coloring ability of the colorant is required for holding the color reproducing ability of the original image.

As the method for dissolving the drawbacks of the pigment, a means by which a dispersed pigment particle diameter of submicron order of primary particles without coagulated secondary particles is attained by using a flashing method for improving the transparency and a means by which the electric charging ability, fixing ability and image uniformity are improved by covering the pigment particle by a binder resin and a shell resin are proposed, cf. Patent Document 3. However, sufficient transparency is difficulty obtained by the use of pigment toner even when the image is output by the above proposed toner.

Entire colors can be reproduced in principle by subtractive color mixing of three colors of yellow, magenta and cyan by the color image forming apparatus. In practice, however, many problems are leaved for correctly reproduce the color of the original image since reproducible range and the chromaticness of the color are lowered depending on the color mixing ability when the toners different in the color are overlapped.

On the other hand, a toner using a dye, cf. Patent Document 4, and that using a mixture of dye and pigment are disclosed. However, the toner using the dye is superior in the transparency and the chromaticness because the dye is in the dissolved state in the binder resin but has drawbacks such as that the light fastness and thermal resistivity are considerably inferior to the pigment.

Relating to the thermal resistivity, problems are caused that contamination in the apparatus by the sublimation of the dye tends to be caused on the occasion of fixing by a heating roller and the dye is dissolved in silicone oil to be used on the occasion of the fixing and finally adheres onto the heating roller so as to cause offset phenomenon additionally to the density lowering by the decomposition of the dye. For dissolving such the drawbacks of the dye, a means for making compatibility of the light fastness, sublimation and the color reproducibility, a means by using a specific anthraquinone dye or a chelate dye is proposed, cf. Patent Document 5. In the case of the toner using the dye, however, sufficient thermal resistivity (sublimation property), light fastness and color reproducibility can be difficulty obtained even when the image is output by using the toner proposed in the above, and the development of a toner satisfying the above conditions is demanded.

It can be considered that the properties are improved by adding an additive, cf. Patent Document 6. However, the stability of the additive itself is required in such the case. In all the cases, the stability of the dye and the additive is important required item but sufficient dissolving means is not obtained yet.

Patent Document 1: U.S. Pat. No. 2,297,691
Patent Document 2: JP B S42-23910
Patent Document 3: JP A H11-160914
Patent Document 4: JP A H05-11504
Patent Document 5: JP Patent No. 3567403
Patent Document 6: JP A 2007-34254

SUMMARY

The invention is attained for solving the above problems and an object of that is to provide an excellent electrophotographic toner improved in the resistivity against heat and humidity and the light fastness by adding additives which are stable and not depended on the property of liquid on the occasion of the toner production.

The object of the invention is attained by the following means.

A copper complex compound represented by the following Formula (1).

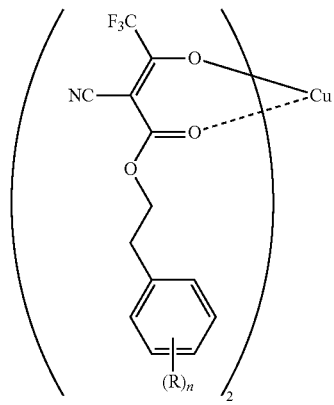

Formula (1)

In the formula (1), groups represented by R is a substituent, n is an integer of from 1 to 5 and the total carbon number contained in (R)n is 14 or more.

The copper complex compound is suitably used for an electrophotographic toner.

Characteristics of the copper compound of the invention is that the compound is stable itself, and the electrophotographic toner is characterized in that the stability of the dye is further raised by coexistence of a specific structured dyer contained in the thermoplastic resin, hereinafter referred to as the binder resin, and the specific structured copper compound.

The electrophotographic toner superior in the transparency, particularly in the color reproducibility, and in the light fastness and resistivity against heat and humidity without considering relating to the effect of liquid property variation of the liquid and the image forming method using such the electrophotographic toner can be provided by the invention.

DESCRIPTION OF THE PREFERRED EMBODIMENT

Figure 1:
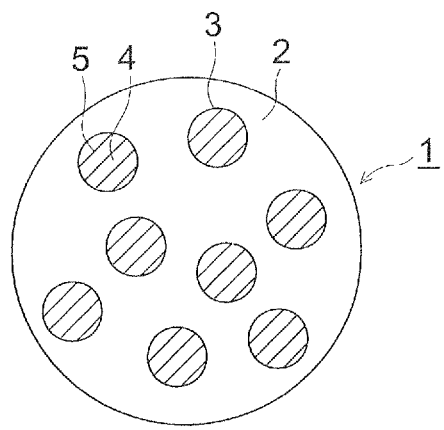
FIG. 1 shows a schematic cross section of a toner particle in which colored fine particles are dispersed in a thermoplastic resin.
Figure 2:
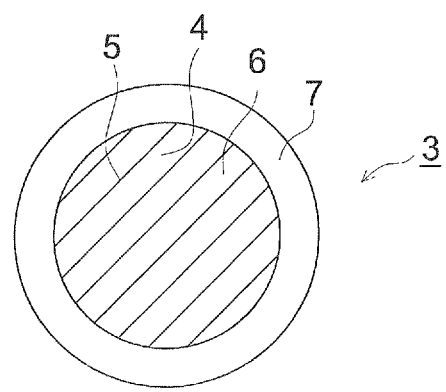
FIG. 2 shows a schematic cross section of a colored particle having a core/shell structure constituted by an inner core covered with an outer shell.

As a result of investigation by the inventors, the dye represented by a copper complex compound represented by Formula (1) is found out and it is found that the color toner comprising the thermoplastic resin containing the metal complex compound shows excellent chromaticness and image fastness.

The electrophotographic toner shows excellent chromaticness and image fastness by incorporating the dye represented by the formula (2) into the copper complex compound represented by the formula (1).

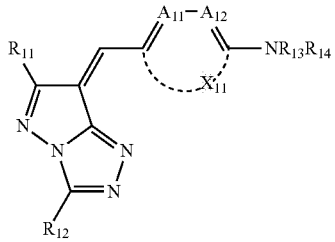

Formula (2)

$R_{11}$ and $R_{12}$ are each independently a substituent, $R_{13}$ and $R_{14}$ are each independently an alkyl, aryl or heterocyclic group. $A_{11}$ and $A_{12}$ each independently represents =$CR_{15}$— or =N—, $R_{15}$ is a hydrogen atom or a substituent, $X_{11}$ is an atomic group for forming a 5- or 6-member aromatic group together with $A_{11}$ and $A_{12}$ or an atomic group for forming a heterocyclic ring together with $A_{11}$ and $A_{12}$.

The electrophotographic toner comprises a colorant composed of a copper complex compound of Formula (1) and a dye contained in the thermoplastic resin. The dispersing state of the colorant is colored fine particles having a diameter of nanometer-size.

The structure represented by Formula (1) is described below.

<<Compound Represented by Formula (1)>>

In Formula (1), R is independently a substituent and n is an integer of from 1 to 5. The total number of carbon atoms contained in (R)n is 14 or more.

In Formula (1), examples of the substituent represented by R include an alkyl group such as a methyl group, an ethyl group, a propyl group, an isopropyl group, a tert-butyl group, a pentyl group, a hexyl group, an octyl group, a dodecyl group, a tridecyl group, a tetradecyl group, a pentadecyl group and a trifluoromethyl group, a cycloalkyl group such as a cyclopentyl group and a cyclohexyl group, an alkenyl group such as a vinyl group and an allyl group, an alkynyl group such as ethynyl group and a propargyl group, an aryl group such as a phenyl group and a naphthyl group, a heteroaryl group such as a furyl group, a thienyl group, a pyridyl group, a pyridazyl group, a pyrimidyl group, a pyrazyl group; a triazyl group, an imidazolyl group, a pyrazolyl group, a thiazolyl group, a benzimidazolyl group, a benzoxazolyl group, a quinazolyl group and phthalazyl group, a heterocyclic group such as a pyrrolidinyl group, an imidazolidinyl group, a morpholyl group and an oxazolidinyl group, an alkoxyl group such as a methoxy group, an ethoxy group, a propyloxy group, a pentyloxy group, a hexyloxy group, an octyloxy group and a dodecyloxy group, a cycloalkoxyl group such as a cyclopentyloxy group and a cyclohexyloxy group, an aryloxyl group such as a phenoxy group and a naphthyloxy group, an alkylthio group such as a methylthio group, an ethylthio group, a propylthio group, a pentylthio group, a hexylthio group, an octylthio group and a dodecylthio group, a cycloalkylthio group such as a cyclopentylthio group and cyclohexylthio group, an arylthio group such as a phenylthio group and a naphthylthio group, an alkoxycarbonyl group such as a methyloxycarbonyl group, an ethyloxycarbonyl group, a butyloxycarbonyl group, an octyloxycarbonyl group and dodecyloxycarbonyl group, an aryloxycarbonyl group such as a phenyloxycarbonyl group and a naphthyloxycarbonyl group, a sulfamoyl group such as an aminosulfonyl group, a methylaminosulfonyl group, a dimethylaminosulfonyl group, a butylaminosulfonyl group, a hexylaminosulfonyl group, a cyclohexylaminosulfonyl group, an octylaminosulfonyl group, a dodecylaminosulfonyl group, a phenylaminosulfonyl group, a naphthylaminosulfonyl group and a 2-pyridylaminosulfonyl group, an acyl group such as an acetyl group, an ethylcarbonyl group, a propylcarbonyl group, a pentylcarbonyl group, a cyclohexylcarbonyl group, an octylcarbonyl group, a 2-ethylhexylcarbonyl group, a dodecylcarbonyl group, a phenylcarbonyl group, a naphthylcarbonyl group and a pyridylcarbonyl group, an acyloxy group such as an acetyloxy group, an ethylcarbonyloxy group, a butylcarbonyloxy group, an octylcarbonyloxy group, a dodecylcarbonyloxy group and a phenylcarbonyloxy group, an amido group such as a methylcarbonylamino group, an ethylcarbonylamino group, a dimethylcarbonylamino group, a propylcarbonylamino group, a pentylcarbonylamino group, a cyclohexylcarbohylamino group, a 2-ethylhexylcarbonylamino group, an octylcarbonylamino group, a dodecylcarbonylamino group, a phenylcarbonylamino group and a naphthylcarbonylamino group, a carbamoyl group such as an aminocarbonyl group, a methylaminocarbonyl group, a dimethylaminocarbonyl group, propylaminocarbonyl group, a pentylaminocarbonyl group, cyclohexylaminocarbonyl group, an octylaminocarbonyl group, a 2-ethylhexylaminocarbonyl group, a dodecylaminocarbonyl group, a phenylaminocarbonyl group, a naphthylaminocarbonyl group and a 2-pyridylaminocarbonyl group, a ureido group such as a methylureido group, an ethylureido group, a pentylureido group, a cyclohexylureido group, an octylureido group, a dodecylureido group, a phenylureido group, a naphthylureido group and a 2-pyridylureido group, a sulfinyl group such as a methylsulfinyl group, an ethylsulfinyl group, a butylsulfinyl group, a cyclohexylsulfinyl group, a 2-ethylhexylsulfinyl group, a dodecylsulfinyl group, a phenylsulfinyl group, a naphthylsulfinyl group and a 2-pyridylsulfinyl group, an alkylsulfonyl group such as a methylsulfonyl group, an ethylsulfonyl group, a butylsulfonyl group, a cyclohexylsulfonyl group, a 2-ethylhexylsulfonyl group and a dodecylsulfonyl group, an arylsulfonyl group such as a phenylsulfonyl group, a naphthylsulfonyl group and a 2-pyridylsulfonyl group, an amino group such as an amino group, an ethylamino group, a dimethylamino group, a butylamino group, a cyclopentylamino group, a 2-ethylhexylamino group, a dodecylamino group, an anilino group, a naphthylamino group and a 2-pyridylamino group, a cyano group, a nitro group, and a halogen atom such as a fluorine atom, a chlorine atom and a bromine atom. These groups may be substituted by a similar group.

Among them, the alkyl group, aryl group, heterocyclic group, heteroaryl group, alkoxyl group, sulfamoyl group, ureido group, amino group, amido group, acyl group, alkoxycarbonyl group, carbamoyl group, cyano group and halogen atom are preferable, and the alkyl group, alkoxyl group, amido group and halogen atom are more preferable, and the alkoxyl group is most preferable. A straight alkoxy group is further preferable.

In Formula (1), n is an integer of from 1 to 5 and is preferably 1 from the viewpoint of easiness of synthesis.

In Formula (1), the total number of carbon atoms contained in (R)n is not less than 14, preferably not less than 16, and more preferably not less than 18. The total number of carbon atoms contained in (R) is preferably not more than 50.

In Formula (1), log P of one molecule of the ligand is preferably not less than 9. When the log P value is within this range, it can be surmised that the copper complex compound is excellent in the stability against water, particularly in the anti-hydrolysis in an acid region so as to sufficiently realize the essential function of it.

The log P is a parameter expressing degree of the hydrophilicity-hydrophobicity of the compound and higher value corresponds to higher hydrophobicity and lower value corresponds to higher hydrophilicity. The log P value is well known parameter of compound and can be obtained by measurement or calculation.

The value of log P calculated by the following expression may be different a little from the value determined by measurement in some cases. However, the difference is not so large and approximate property of the compound can be sufficiently surmised by measurement or calculation. The log P value is preferably determined by the calculation when the value can be determined by each of the methods.

$$\log P_{O/W}$$

$$P_{O/W} = S_O/S_W$$

$S_O$=Solubility of the organic compound in n-octanol at 25° C.

$S_W$=Solubility of the organic compound in purified water at 25° C.

For determining the logP value by calculation, some methods such as a method based on molecular orbital calculation, a fragment method basically utilizing data of Hansch and a method by HPLC a re applicable. In the invention, the calculation is preferably carried out by using PROJECT LEADER contained in a molecular calculation package CAChe manufactured by FUJITSU or CHEMPROP contained in a chemical structure drawing software CS CHEM DRAW 8.0 manufactured by CAMBRIDGE SOFT, and the calculation by CHEM PROP in CS CHEM DRAW 8.0 or its later version is particularly preferable .

In the invention, the value calculated, by CHEMPROP in CS CHEM DRAW is used.

The ligand in Formula (1) can take keto-enol structures represented by 1a and 1b and the log P value calculated as to Formula (1a) is used.

Formula (1a) ↔ Formula (1b)

Typical concrete examples of the copper complex compound are listed below. The structure shown below is only one canonical structure among plural resonance structures capable of being taken by the compound, and the distinction between the covalent bond represented by a straight line (–) and the coordination bond represented by dotted line ( . . . ) is superficial and not absolute distinction.

Ar(bonding at *)

(1)-1  *—C₆H₄—C₁₄H₂₉(n)

(1)-2  *—C₆H₄—C₁₆H₃₃(n)

(1)-3  *—C₆H₃(2-C₂H₅)—C₁₂H₂₅(n)

(1)-4  *—C₆H₃(2-C₂H₅)—C₁₄H₂₉(n)

(1)-5  *—C₆H₄—NHCOC₁₇H₃₅(n)

(1)-6  *—C₆H₄—NHCOC₁₄H₂₉(n)

(1)-7  *—C₆H₃(2-CH₃)—NHCOC₁₇H₃₅(n)

(1)-8  *—C₆H₃(2-Cl)—NHCOC₁₇H₃₅(n)

(1)-9  *—C₆H₄(3-Cl, NHCOC₁₇H₃₅(n))

(1)-10  *—C₆H₄—NHSO₂C₁₆H₃₃(n)

(1)-11  *—C₆H₂(2,6-(CH₃)₂)—NHSO₂C₁₈H₃₇(n)

(1)-12  *—C₆H₄—N(C₈H₁₇(n))₂

(1)-13  *—C₆H₄—N(C₁₀H₂₁(n))₂

(1)-14  *—C₆H₄—N(C₄H₉)(COC₁₇H₃₅(n))

(1)-15  *—C₆H₄—OC₁₄H₂₉(n)

(1)-16  *—C₆H₄—OC₁₆H₃₃(n)

(1)-17  *—C₆H₄—OC₁₈H₃₇(n)

(1)-18  *—C₆H₄—OC₂₀H₄₁(n)

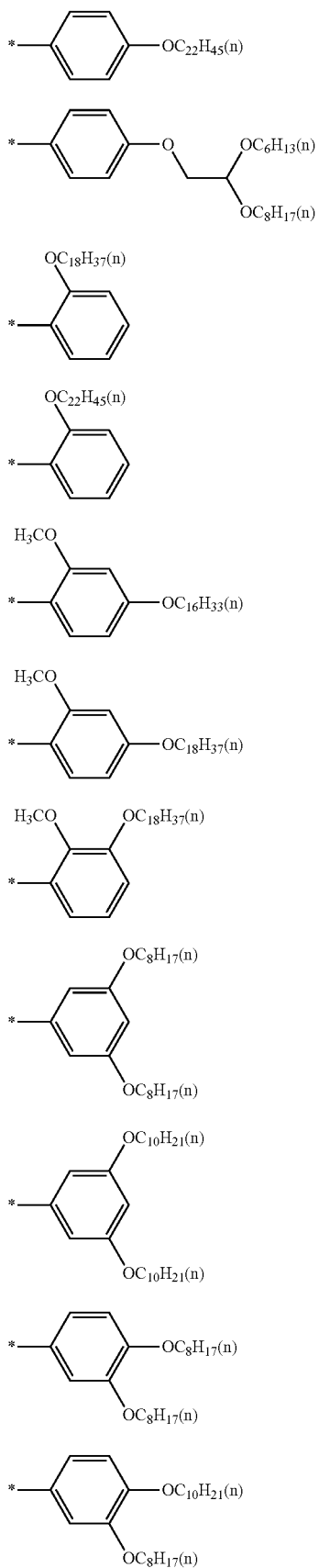
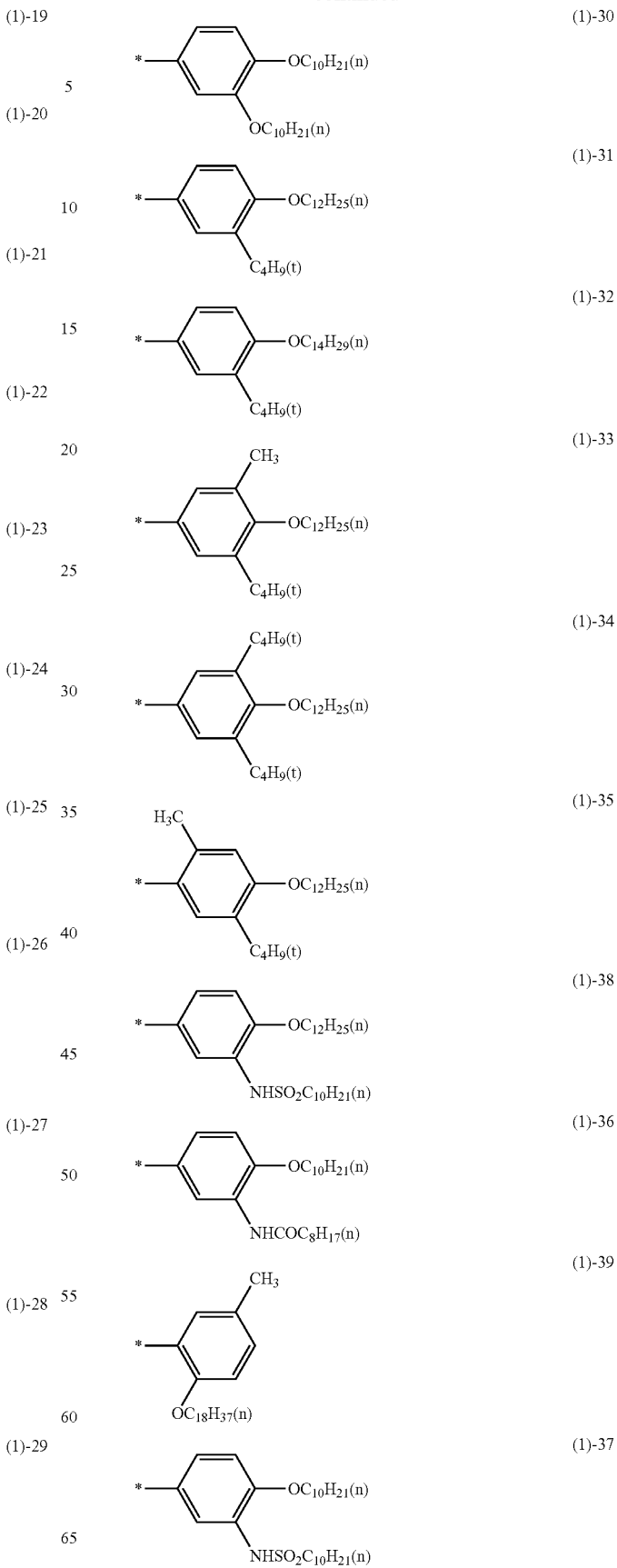

-continued

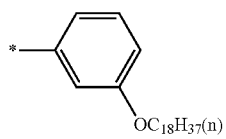
(1)-40

The copper complex compounds represented by Formula (1) and the ligands can be synthesized referring JP A 2002-332259, JP A 2003-237246 and JP A 2007-31425.

The copper complex compounds represented by Formula (1) can be synthesized by ligand exchanging the ligand and a copper compound as described in JP A 2007-31425.

As such the copper compound, for example, copper acetate, copper stearate, copper 2-ethylhexanate, copper sulfate and cupric chloride are cited which are easily available on the market.

Examples of the copper complex compound represented by Formula (1) are concretely described below. Other compounds can be synthesis in the similar manner and the method is not limited to the below.

<<Synthesis of Exemplified Compound 1-17>>

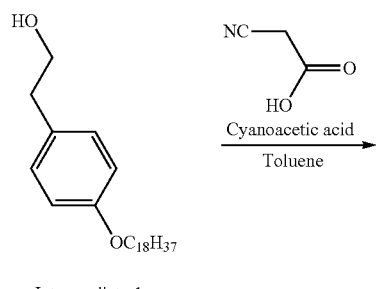

Intermediate 1

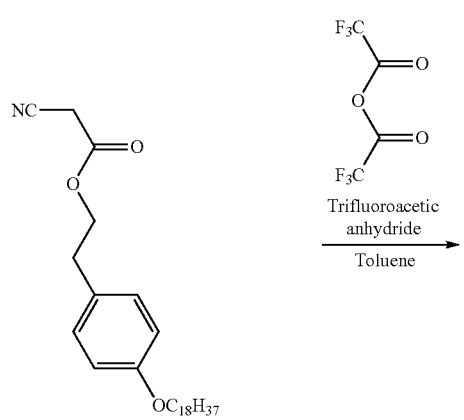

Intermediate 2

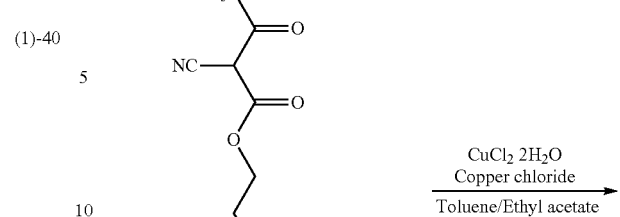

Intermediate 3

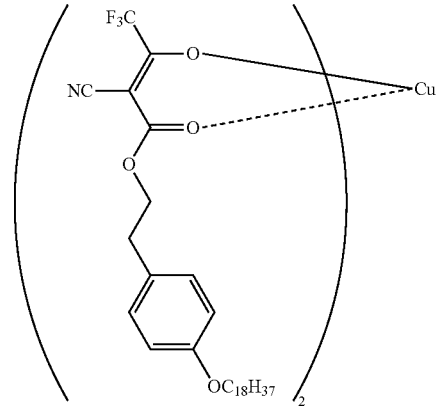

Exemplified Compound 1-17

<Synthesis of Intermediate 2>

To 15.00 g of Intermediate 1, 3.59 g of cyanoacetic acid and 0.2 g of p-toluenesulfonic acid, 45 ml of toluene was added and made react for 2 hours by heating and refluxing while dehydrating by an esterifying tube. Then the reacting liquid was cooled and washed for three times by adding water, and the solvent was removed by distillation under reduced pressure. Thus 17.8 g of slightly brownish liquid was obtained. It is confirmed that the obtained material was the objective substance by identification by MASS, H-NMR and IR spectrum.

<Synthesis of Intermediate 3>

To 18.7 g of Intermediate 2, 88 ml of toluene was added and then 8.52 g of calcium chloride was added and the interior temperature was cooled by 15° C. by ice water. After that, 11.66 g of triethylamine was added and 8.87 g of trifluoroacetic anhydride was dropped while maintaining the temperature. After completion of the dropping, 40 ml of water was added for washing and the solvent was removed by distillation. The product was recrystallized by diisopropyl ether. Thus 20.2 g of milky-white crystals of Intermediate 3 were obtained. It was confirmed that the obtained material was the objective substance by identification by MASS, H-NMR and IR spectrum.

<Synthesis of Exemplified Compound 1-17>>

Nineteen point one three grams of Intermediate 3 was dissolved by adding 80 ml of toluene and 16.2 ml of ethyl acetate. Then a solution prepared by dissolving 2.94 g of copper chloride in 16.2 ml of water was dropped and the system was stirred for 1 hour after completion of the dropping. The reacting liquid was heated for dissolving the product and the product was recrystallized. Thus 6.78 g of milky-green crystals of Exemplified Compound 1-17 were obtained.

<<Synthesis of Exemplified Compound 1-5>>

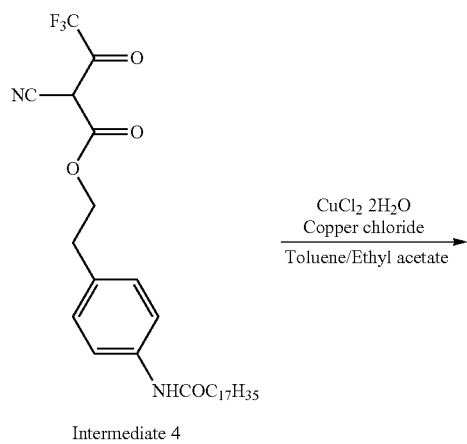

Intermediate 4

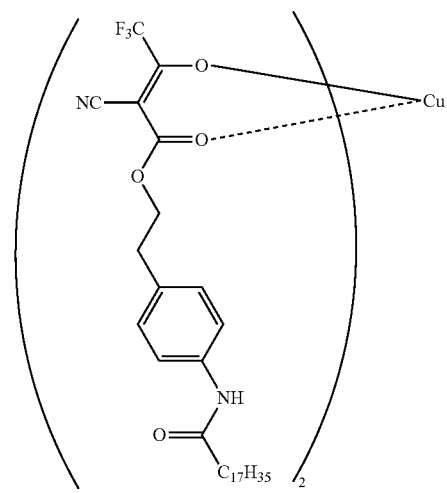

Exemplified Compound 1-5

In 80 ml of toluene and 16.2 g of ethyl acetate 19.58 grams of Intermediate 4 was dissolved by heating. Then a solution prepared by dissolving 2.94 g of copper chloride in 16.2 ml of water was dropped and the system was stirred for 1 hour after completion of the dropping. The reacting liquid was heated for dissolving the product and the product was recrystallized. Thus 16.93 g of milky-green crystals of Exemplified Compound 1-5 were obtained. It was confirmed by determination of copper by ICP and IR spectrum that the obtained product was the objective substance.

It is preferable to employ a compound represented by Formula (2) in combination of a copper compound represented by Formula (1).

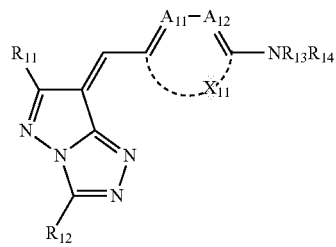

Formula (2)

<<Compound Represented by Formula (2)>>

In Formula (2), $R_{11}$ and $R_{12}$ are each independently a substituent, $R_{13}$ and $R_{14}$ each independently represents an alkyl group, aryl group or heterocyclic group. $A_{11}$ and $A_{12}$ are each independently $=CR_{15}$— or $=N$—, $R_{15}$ is an atomic group for forming a hydrogen atom or a substituent, $X_{11}$ is a 5- or 6-member aromatic group together with $A_{11}$ and $A_{12}$ or an atomic group for forming a heterocyclic ring together with $A_{11}$ and $A_{12}$.

The substituents represented by $R_{11}$ and $R_{12}$ of Formula (2) are the same as R in the Formula (1), and preferable examples thereof include an alkyl group, an aryl group, a heterocyclic group, a heteroaryl group, an alkoxy group, a sulfamoyl group, a ureido group, an amino group, an amido group, an acyl group, an alkoxycarbonyl group, a carbamoyl group, a cyano group, and a halogen atom. More preferably, an alkyl group, an aryl group, an alkoxycarbonyl group and a carbamoyl group are mentioned.

It is preferable to contain a substituent which changes a spectroscopic absorbance wave shape by an interaction with a copper compound represented by Formula (1). Preferable examples thereof include an alkoxy or alkyl group containing an oxygen atom or a nitrogen atom.

$R_{13}$ and $R_{14}$ in the Formula (2) are preferably an alkyl or aryl group, and more preferably an alkyl group, particularly that having 4 to 12 carbon atoms. It is preferred $R_{13}$ and $R_{14}$ are same.

It is preferable that at least one of $A_{11}$ and $A_{12}$ is $=CR_{15}$—.

The substituent represented by $R_{15}$ is the same as R in the Formula (1), and preferable examples thereof include an alkyl group, an aryl group, an alkoxy group, an amino group, an amido group, a carbamoyl group and a halogen atom. More preferably an alkyl group, an alkoxy group and a halogen atom are mentioned. The particularly preferable example is a hydrogen atom or an alkyl group for $R_{15}$.

Examples of the aromatic group and the heterocyclic ring for $X_{11}$ include a benzene ring, a naphthalene ring, a pyridine ring, a pyrazine ring, a furan ring, a thiophene ring, an imidazole ring and a thiazole ring, and more preferably a benzene ring, a pyridine ring a furan ring and a thiophene ring, and particularly preferable examples are a benzene ring and a thiophene ring.

Practical examples of compound represented by Formula (2) are listed, and isomers thereof are included if any. These compounds can be synthesized in accordance with the description of JP A H06-250357, JP A H07-175187 and JP A H10-60296.

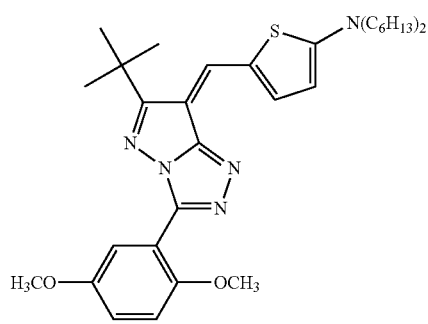
(2)-1
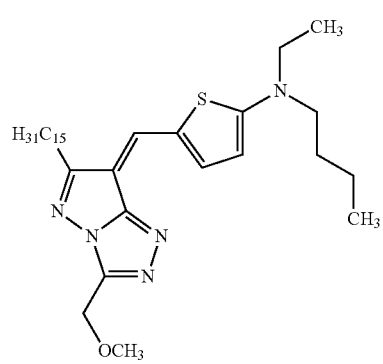
(2)-2
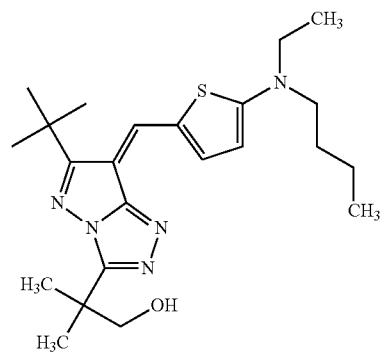
(2)-3
(2)-4
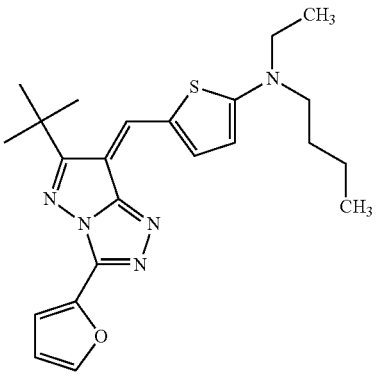
(2)-5
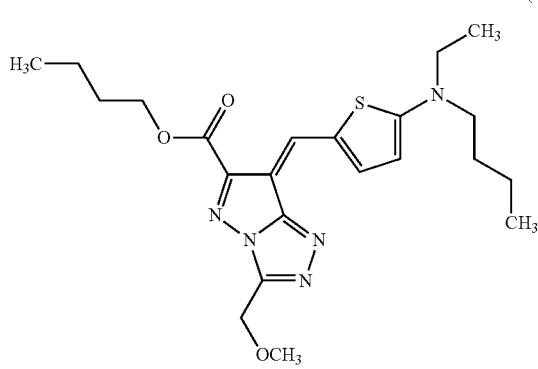
(2)-6
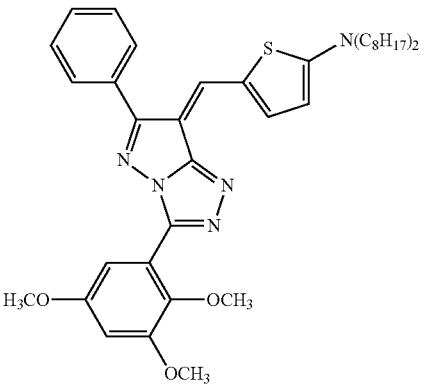
(2)-7
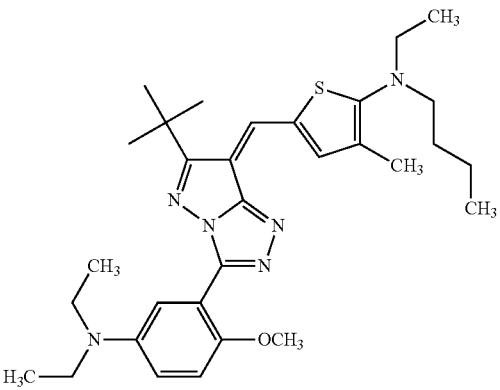
(2)-8

-continued
(2)-9
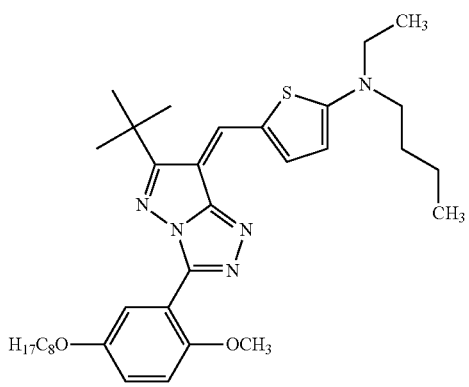
(2)-10
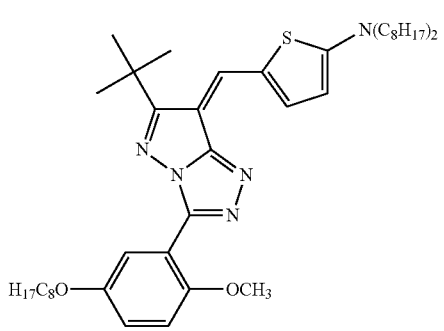
(2)-11
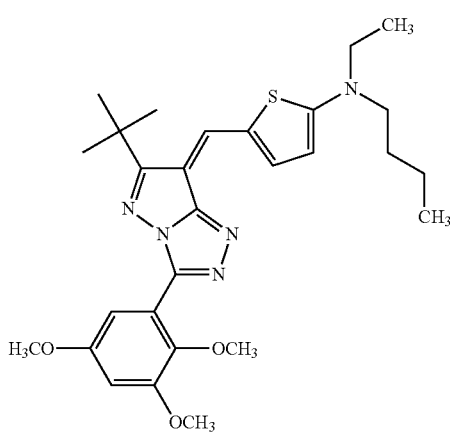
(2)-12
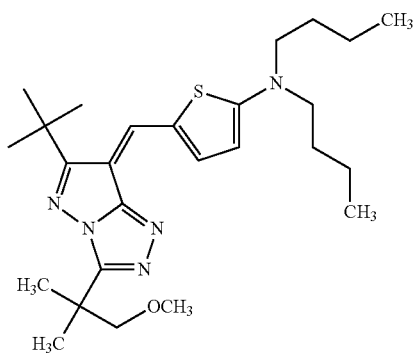
-continued
(2)-13
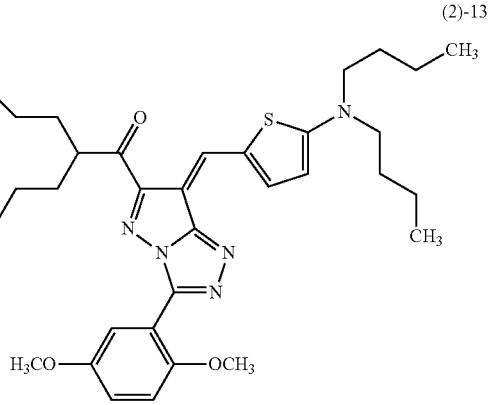
(2)-14
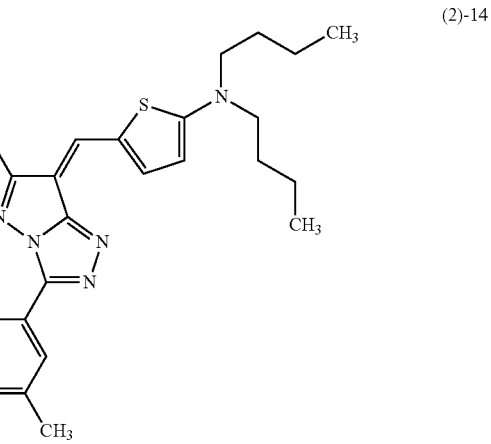
(2)-15
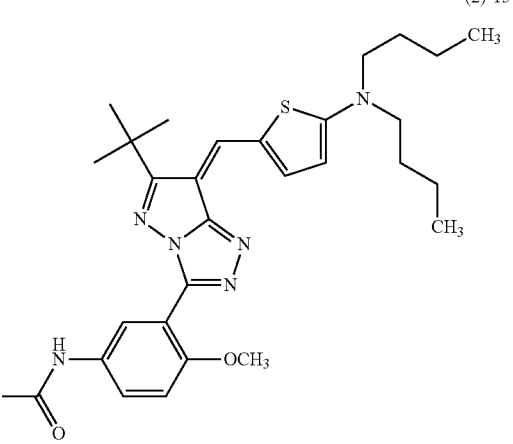

-continued
(2)-16
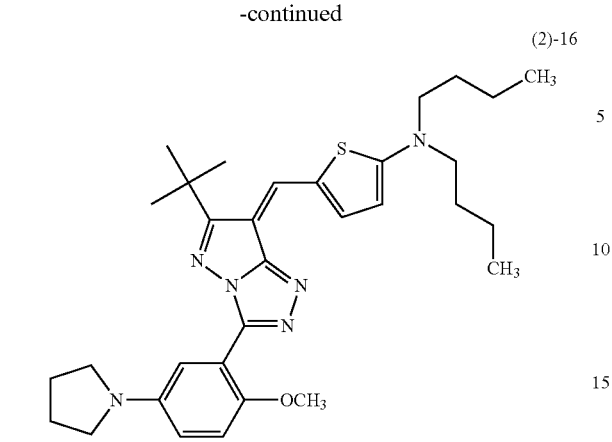
(2)-17
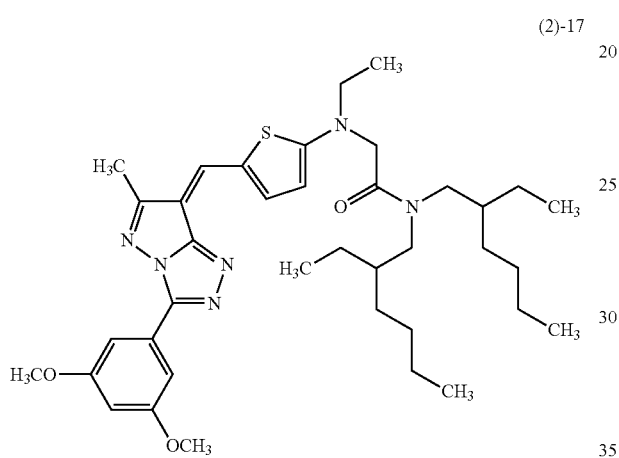
(2)-18
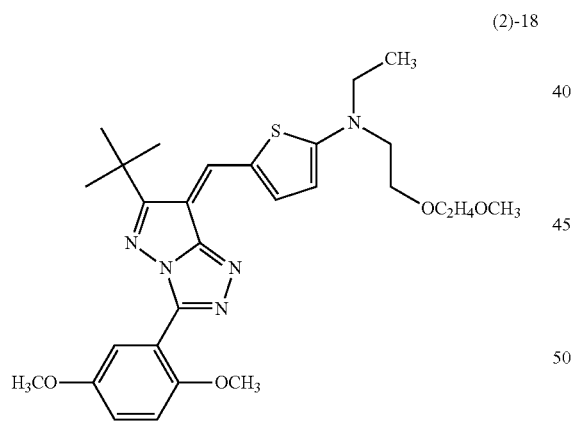
(2)-19
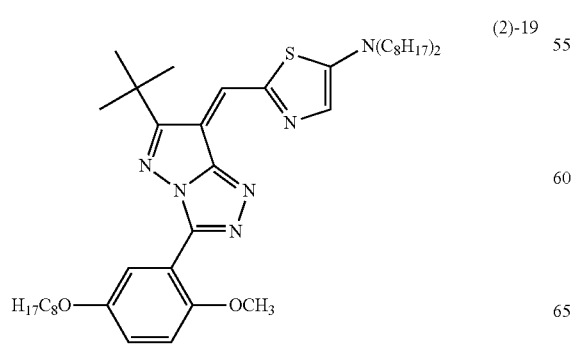
-continued
(2)-20
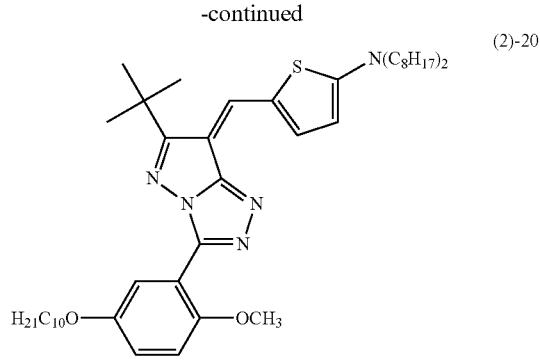
(2)-21
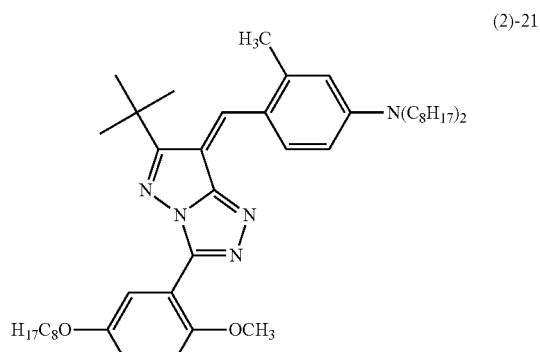
(2)-22
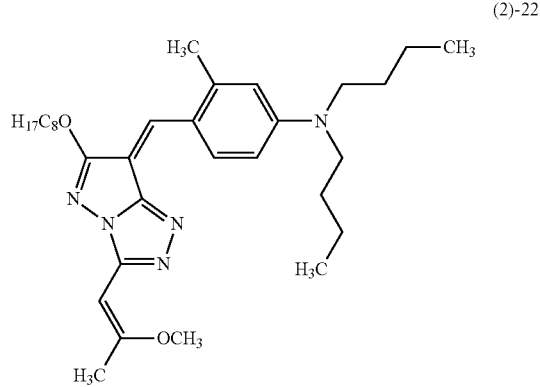
(2)-23
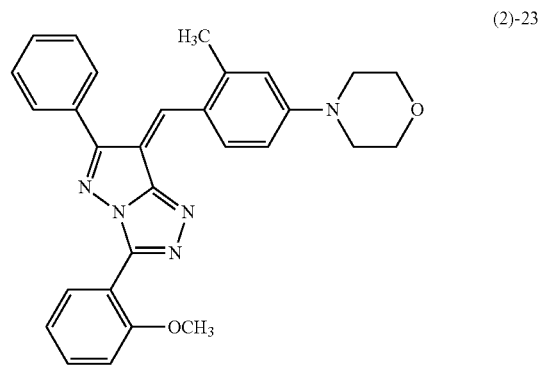

-continued

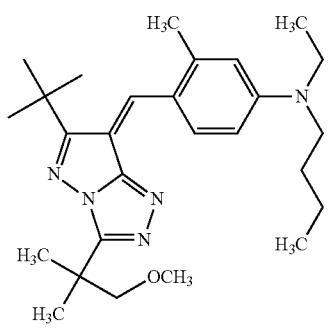
(2)-24

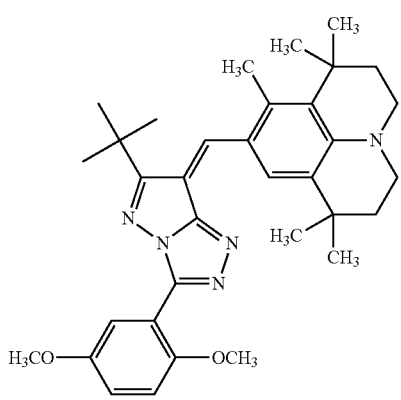
(2)-25

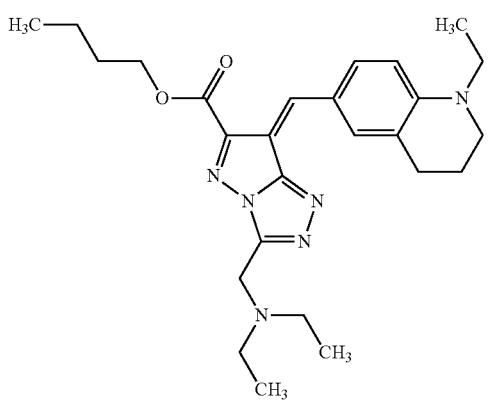
(2)-26

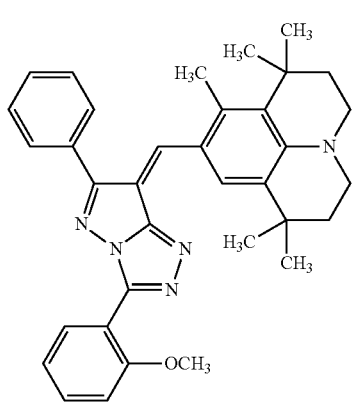
(2)-27

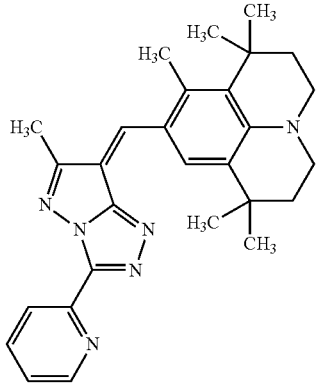
(2)-28

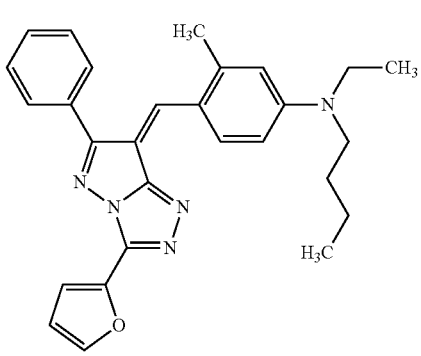
(2)-29

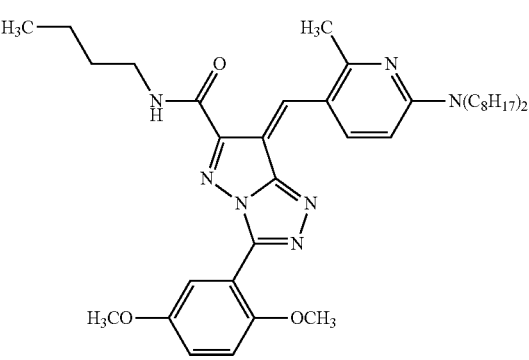
(2)-30

The electrophotographic toner of the invention is described below.
(Dispersing Method of Dye)

The electrophotographic toner of the invention can be produced by that a dye dispersion liquid is directly dispersed in a binder resin or mixed with a colored fine particle dispersion and a later-mentioned desired additive is added and then the resulted material is subjected to various methods such as a knead-crashing method, suspension polymerization method, emulsion polymerization method, emulsifying dispersion particle producing method and encapsulating method. Among these methods, the emulsion polymerization method is preferred from the viewpoint of the cost and the production stability of the producing when the particle size reducing for rising in the image quality is considered. In the emulsion polymerization method, a thermoplastic resin emulsion prepared by emulsion polymerization is mixed with a dispersion of toner particle component such as a dispersion of solid particles of dye and particles are formed by controlling pH. The resultant particles are gradually associated while taking balance between the repulsion force of the surface of formed particle and the coagulating force caused by the addition of electrolyte. The association is carried out while controlling the size and shape of the particle and the inter-particle fusion and shape of the associated particle are controlled by stirring and heating to produce the toner particle.

When the dye dispersion is prepared by direct dispersion, the dispersion can be carried out by using a usually roller kneading disperser, a beads dispersing machine, a high speed stirring dispersing machine or a medium type stirrer. The dispersion can be also prepared by a method the same as the following method for producing the colored fine particle dispersion. Namely, the dye is dissolved (or dispersed) in an organic solvent and emulsified in water and then the organic solvent is removed.

In the electrophotographic toner, the colored particles can be dispersed in the thermoplastic resin. The colored fine particle contains at least one kind of the metal complex compound represented by Formula (1) or the dye represented by Formula (2). The dispersed particle diameter can be controlled by using a dispersing method such as the later-mentioned dry-in-liquid method. The electrophotographic toner of the invention may further contain a resin different in the composition from the thermoplastic resin or a high-boiling solvent. In the toner using the above dye, the colored fine particles (including simply dispersed dye) can be dispersed in the thermoplastic resin instead of directly dispersing or dissolving of dye into the toner binder resin such as the method applied for usually known toner using a dye.

The dye in the colored fine particle is dissolved in the resin at the level of molecule state; therefore a light insulation component insulating light in the toner such as a concealing particle can be removed. Accordingly, it is considered that the transparency of each of mono-color images is increased so that the transparence of overlapped color image is also improved.

FIG. 1 schematically shows the cross section of an electrophotographic toner particle of the invention. The colored fine particles 3 each containing the resin 4 and dye 5 are dispersed in the thermoplastic resin 2. In an example of preferable embodiments, the colored fine particle may be covered by a resin shell 7. In such the case, combination of the resin constituting the core 6 of the colored fine particle and the thermoplastic resin (binder resin) is not specifically limited and the degree of selection freedom of the material is made large. When the shell resins of the four color (yellow, magenta, cyan and black) toners are the same, advantage in the cost is large since the toners can be produced under the same production condition. Moreover, anxieties of the sublimation of the dye and contamination of oil, which are generally considered as problems in toners using dye, are not caused since transfer of the dye as the colorant to outside of the colored fine particle (exposing of the dye at the surface of the colored fine particle) is not caused when the colored fine particle is covered by the shall resin.

(Production Method of Colored Fine Particle)

An example of production method as one of preferable embodiments of the invention is described below.

For instant, the colored fine particle can be obtained by dissolving or dispersing the dye (or the dye, resin, high-boiling solvent and additive) in an organic solvent and emulsifying in water and then removing the solvent; such the method is called as the dry-in-liquid method. When the resin is added for forming the resin shell, a monomer having a polymerizable unsaturated double bond is added to the colored fine particle and emulsion polymerization is carried out in the presence of a surfactant to precipitate the resin simultaneously with polymerization. Thus colored fine particle having the core/shell structure can be obtained Other than that, such the colored fine particle can be prepared by various methods such as a method in which an aqueous dispersion of rein fine particles is previously prepared by emulsion polymerization and mixed with an organic solvent solution of the dye for impregnating the dye into the resin fine particle and then the shell is formed on the core of such the colored fine particle.

The shell preferably formed by an organic resin, and a method is applicable in which a resin dissolved in an organic solvent is gradually propped for simultaneously precipitating and adsorbing onto the colored fine particle surface. In the invention, the method is preferable in which the colored particle to be used as the core is formed and then the monomer having a polymerizable unsaturated double bond is added and emulsion polymerization is carried out in the presence of the surfactant for forming the shell by precipitating the resin simultaneously with the polymerization.

Other than the above, the dye may be dispersed in water in the presence of the surfactant by a beads disperser, a high speed stirring dispersing machine or a medium using type stirrer.

(Surfactant)

A usual anionic emulsification agent (surfactant) and/or nonionic emulsification agent (surfactant) can be used according to necessity on the occasion of emulsification of the colored fine particle as one of preferable embodiments of the invention.

As examples of nonionic surfactant, a polyoxyethylene alkyl ether such as polyoxyethylene lauryl ether and polyoxyethylene stearyl ether, a polyoxyethylene alkylphenyl ether such as polyoxyethylene nonylphenyl ether, a sorbitan higher fatty acid ester such as sorbitan monolaurate, sorbitan monostearate and sorbitan trioleate, a polyoxyethylene higher fatty acid ester such as polyoxyethylene monolaurate and polyoxyethylene monostearate, a glycerol higher fatty acid ester such as oleic monoglyceride and stearic monoglyceride and a polyoxyethylene-polyoxypropylene block copolymer are cited.

As examples of the anionic surfactant, a higher fatty acid salt such as sodium oleate, an alkylarylsulfonate such as sodium dodecylbenzenesulfonate, an alkylsulfate such as sodium laurylsulfate, a polyoxyethylene alkyl ether sulfate such as sodium polyethoxyethylene lauryl ether sulfate, a polyoxyethylene alkylaryl ether sulfate such as sodium polyoxyethylene nonylphenyl ether sulfate, a salt of alkylsulfosuccinic ester salt such as sodium monooctyl-sulfosuccinate, sodium dioctylsulfosuccinate and sodium polyoxyethylene laurylsulfosuccinate and a derivative thereof can be cited.

(Dye)

The dyes to be used in the invention are described below.

The dyes represented by Formula (2) are characteristically used in the invention and the dye may be used singly or in combination with another dye according to necessity. Usually known dyes may be used together with the dye represented by Formula (2) and an oil-soluble dye is preferable in the invention. The oil-soluble dye is generally a dye having no water-soluble group such as a carboxyl group and a sulfonic acid group and soluble in an organic solvent and insoluble in water, and includes a water-soluble dye which can be given oil solubility by making a salt with a long-chain base, for example, salt making dyes formed by an acid dye, direct dye or reactive dye with a long-chain amine.

The following dyes can be exemplified: VALIFAST Yellow 4120, VALIFAST Yellow 3150, VALIFAST Yellow 3108, VALIFAST Yellow 2310N, VALIFAST Yellow 1101, VALIFAST Red 3320, VALIFAST Red 3304, VALIFAST Red 1306, VALIFAST Blue 2610, VALIFAST Blue 2606, VALIFAST Blue 1603, Oil Yellow GG-S, Oil Yellow 3G, Oil Yellow 129, Oil Yellow 107, Oil Yellow 105, Oil Scarlet 308, Oil Red RR, Oil red OG, Oil Red 5B, Oil Pink 312, Oil Blue BOS, Oil Blue 613, Oil Blue 2N, Oil Black BY, Oil Black BS, Oil Black 860, Oil Black 5970, Oil Black 5906 and Oil Black 5905 each manufactured by Orient Chemical Industry Ltd., Kayaset Yellow SF-G, Kayaset Yellow K-CL, Kayaset Yellow GN, Kayaset Yellow A-G, Kayaset Yellow 2G, Kayaset Red SF-4G, Kayaset Red K-BL, Kayaset Red A-BR, Kayaset Magenta 312 and Kayaset Blue K-FL each manufactured by Nippon Kayaku Co., Ltd., FS Yellow 1015, FS Magenta 1404, FS Cyan 1522, FS Blue 1504, C. I. Solvent Yellow 88, 83, 82, 79, 56, 29, 19, 16, 14, 04, 03, 02 and 01, C. I. Solvent Red 84:1, 84, 218, 132, 73, 72, 51, 43, 27, 24, 18 and 01, C. I. Solvent Blue 70, 67, 44, 40, 35, 11, 02 and 01, C. I. Solvent black 43, 70, 34, 29, 27, 22, 7 and 3, C. I. Solvent Violet 3, C. I. Solvent green 3, Plast Yellow DY352 and Plast Red 8375 each manufactured by Arimoto Chemical Co., Ltd., MS Yellow HD-180, MS Red G, MS Magenta HM-1450H and MS Blue HM-1384 each manufactured by Mitsui Chemicals Inc., ES Red 3001, ES Red 3002, ES Red 3003, TS Red 305, ES Yellow 1001, ES Yellow 1002, TS Yellow 118, ES Orange 2001, ES Blue 6001 and TS Turq Blue 618 each manufactured by Sumitomo Chemical Co., Ltd., and MACROLEX Yellow 6G, Ceres Blue, GNNEOPAN Yellow O75, Ceres Blue GN and MACROLEX Red Violet R each manufactured by Bayer AG.

A dispersion dye can be used as the oil-soluble dye, and examples of which include C. I. Disperse Yellow 5, 42, 54, 64, 79, 82, 83, 93, 99, 100, 119, 122, 124, 126, 160, 184:1, 186, 198, 199, 204, 224 and 237, C. I. Disperse Orange 13, 29, 31:1, 33, 49, 54, 55, 66, 73, 118, 119 and 163, C. T. Disperse red 54, 60, 72, 73, 86, 88, 91, 92, 93, 111, 126, 127, 194, 135, 143, 145, 152, 153, 154, 159, 164, 167:1, 177, 181, 204, 206, 207, 221, 239, 240, 258, 277, 278, 283, 311, 323, 243, 348, 356 and 362, C. I. Disperse Violet 33, C. I. Disperse Blue 56, 60, 73, 87, 113, 128, 143, 148, 154, 158, 165, 165:1, 165:2, 176, 183, 185, 197, 198, 201, 214, 224, 225, 257, 266, 287, 354, 358, 365 and 368, and C. I. Disperse Green 6:1 and 9.

Other than the above, cyclic methylene compounds such as phenols, naphthols, pyrazolone and pyrazolotriazole, azomethine dye derived from a coupler such as an open chain methylene compound and an indoaniline dye are also preferably usable.

The dyes described in JP A H03-114892, JP A H04-62092, JP A H04-62094, JP A H04-82896, JP A H05-16545, JP A H05-177958 and JP A H05-301470 are preferable.

(Particle Diameter)

The colored fine particle as one of preferable embodiments of the invention preferably has a volume average particle diameter of from 10 nm to 1 µm. When the volume average particle diameter is less than 10 nm, the effect of sealing the dye in the polymer of the colored fine particle is lowered and the stability of the colored fine particle tends to be degraded and the storage stability is tends to be lowered because the surface area per unit volume of the particle becomes very large. Besides, a large particle having a size exceeding 1 µm is easily precipitated in the course of fine particle production so that the stability in accumulation is lowered. Moreover, decreasing in the glossiness and considerable lowering in the transparency are caused when such the particle is used to make the toner. Accordingly, the average particle diameter of the colored fine particle is preferably from 10 nm to 1 µm, more preferably from 10 to 500 nm, and further preferably from 10 to 100 nm.

The volume average particle diameter can be determined by a dynamic light scattering method, laser diffraction method, centrifugal precipitation method, FFF method or electric sensor method. In the invention, the particle diameter is preferably determined by the dynamic light scattering method using ZETASIZER, manufactured by Malvern Ltd.

(Dye Content)

The colored fine particle relating to the invention preferably has a dye content of from 10 to 70% by weight. When the dye content is from 10 to 70% by weight, sufficient density can be obtained and the protection effect of the resin to the dye is realized so that the storage stability of the fine particle dispersion is superior, therefore the increasing in the particle sized caused by coagulation can be prevented.

(Content of Copper Complex Compound)

The copper complex compound represented by Formula (1) may be used singly or in combination of two kinds, and the total amount of the copper complex compounds is preferably from 0.8 to 3 times, and more preferably 1 to 2 times, in mole of a compound represented by Formula (1) or a dye. The light fastness is considerably improved when the content is 0.8 times or more and the dispersion stability of the colored fine particle is raised when the content is 3 times or less so that toner making can be advantageously carried out tough depending on the kind of dye.

(Toner)

In the electrophotographic toner of the invention, a charge controlling agent and an offset preventing agent can be added additionally to the above thermoplastic resin and the colored fine particle.

As the charge controlling agent to be used in the color toner, a colorless, white or faint color charge controlling agent which does not give bad influence on the tone and transparency of the toner can be used. For example, complexes of metal such as zinc and chromium with a derivative of salicylic acid, calixarene type compounds, organic boron compounds and fluorine-containing quaternary ammonium salt type compounds are suitably can be used. For example, the salicylic acid metal complexes described in JP A S53-127726 and 62-145255, the calixarene compounds described in JP A H02-201378, the organic boron compounds described in JP A H02-221967 and the fluorine-containing quaternary ammonium salt type compounds described in 3-1162 are usable. When such the charge controlling agent is used, the content of it is preferably from 0.1 to 10, and more preferably from 0.5 to 5.0, parts by weight to 100 parts by weight of the thermoplastic resin (binder resin).

The offset preventing agent is not specifically limited and polyethylene wax, oxide type polyethylene wax, Carnauba wax, polypropylene wax, oxide type polypropylene wax, Sasol wax, rice wax, candelilla wax, jojoba oil wax and beeswax are usable for example. The adding amount of such the wax is desirably from 0.5 to 5, preferably from 1 to 3, parts by weight to 100 parts by weight of the thermoplastic (binder) resin. The effect of addition is made insufficient when the adding amount is less than 0.5 parts by weight, and the transparence and color reproduction ability is lowered when the adding amount is more than 5 parts by weight.

As an image stabilizing agent, the compounds described or referred on pages 10 to 13 of JP A H08-29934 may be added and phenol type, amine type, sulfur type and phosphor type compounds available on the market are also cited. An organic and inorganic UV absorbent may be added for the same purpose. As the organic UV absorbent, a benzotriazole compound such as 2-(2'-hydroxy-5-t-butylphenyl)benzotriazole and 2-(2'-hydroxy-3,5-di-t-butylphenyl)benzotriazole, a benzophenone type compound such as 2-hydroxy-4-methoxybenzophenone and 2-hydroxy-4-n-octyloxybenzophenone, and a hydroxybenzoate compound such as phenyl salicylate, 4-t-butylphenyl salicylate, n-hexadecyl 2,5-t-butyl-4-hydroxybenzoate and 2,4-di-t-butylphenyl-3',5'-di-t-butyl-4'-hydroxybenzoate can be cited. As the inorganic UV absorbent, titanium oxide, zinc oxide, cerium oxide, iron oxide and barium sulfate can be cited. The organic UV sorbents are preferable. The UV sorbent preferably has 50%-transparent wavelength range of from 350 to 420 nm and more preferably from 360 to 400 nm. The UV cutting ability is insufficient at the wavelength of shorter than 350 nm and the coloring is increased at the wavelength of longer than 420 nm, therefore, such the UV absorbent is not preferable. The adding amount is preferably within the range of from 10 to 200% by weight of the dye is preferable and that from 50 to 150% by weight is more preferable though the adding amount is not specifically limited.

(Thermoplastic or Binder Resin)

As the thermoplastic resin to be contained in the electrophotographic toner of the invention, one having high contacting ability with the colored fine particle or the copper complex fine particle which are one of the preferable embodiments of the invention, and solvent-soluble one is particularly preferred. A curable resin capable of forming a three dimensional structure is usable when the precursor of the resin is solvent soluble. As the thermoplastic resin, one usually used for toner can be used without any limitation. Examples of the thermoplastic resin include a styrene type resin, an acryl resin such as an alkyl acrylate and alkyl methacrylate, a styrene-acryl type copolymer resin, a polyester type resin, a silicone type resin, an olefin type resin, an amide type resin and an epoxy type resin are suitably used, and the resin having high transparency, low viscosity in melted state and sharp melting property is required for raising the transparency and the color reproducibility of the overlapped image. Styrene type resin, acryl type resin and polyester resin are suitable for the resin having such the properties.

The resin having a number average molecular weight (Mn) of from 3,000 to 6,000, preferably from 3,500 to 5,500, a ratio Mw/Mn of weight average molecular weight Mw to number average molecular weight Mn of from 2 to 6, preferably from 2.5 to 5.5, a glass transition temperature of from 50 to 70° C., preferably from 55 to 70° C., and a softening point of from 90 to 110° C., preferably from 90 to 105° C. is desirably used for the binder resin.

Fixing strength against folding is degraded and damages of the image are caused by peeling off of the toner on the occasion of folding a full color solid image when the number average molecular weight of the binder resin is less than 3,000, and the fixing strength is lowered accompanied with lowering in the thermal melting ability on the occasion of fixing when the number average molecular weight exceeds 6,000. Offset at high temperature is easily caused when Mw/Mn is less than 2, and the sharp melt ability at the time of fixing is lowered and light permeability and color mixing ability on the occasion of full color image formation is degraded when the ratio is more than 6. When the glass transition point is lower than 50° C., the heat resistivity of the toner is made insufficient and coagulation of the toner during storage tends to be caused and when the glass transition point is higher than 70° C., the toner is difficulty melted so that the fixing ability and the color mixing ability on the occasion of full color image formation are lowered. When the softening point is lower than 90° C., high temperature offset is easily caused and when higher than 110° C., light permeability, color mixing ability and glossiness of full color image are lowered.

The electrophotographic toner of the invention can be produced by using the above-described thermoplastic resin, colored fine particle and the other desirable additives, the fine particle may be a mixture of several kinds thereof or single kind for each of the particles, and by applying a method such as a knead and pulverizing method, suspension polymerization method, emulsion polymerization method, emulsified dispersion granule forming method, and capsulation method.

Among these production methods, the emulsion polymerization method is preferable from the viewpoint of the cost and stability of the production considering the size down of the toner particle accompanied with the improvement of image quality.

By the polymerization method, the toner particle is produced as follows; thermoplastic resin emulsion prepared by emulsion polymerization is mixed with the dispersion of another component of toner particle such as the colored fine particles and the particles are gradually coagulated while taking balance between the repulsion force of the particle surface and the coagulation force caused by the addition of electrolyte by pH control, and the fusion and shape of the particles is controlled by heating and stirring the system while controlling the diameter and distribution thereof. It is preferable from the viewpoint of high definition reproduction of image to control the volume average diameter of the electrophotographic toner particle to 4 to 10 μm, more preferably to 6 to 9 μm.

In the electrophotographic toner of the invention, a post treatment agent can be added and mixed for providing fluidity and improvement of cleaning suitability. As such the post treatment agent, an inorganic oxide fine particle such as a silica fine particle, an alumina fine particle and a titania fine particle, an inorganic stearic acid compound such as aluminum stearate fine particle and zinc stearate fine particle and an inorganic titanic acid compound fine particle such as strontium titanate and zinc titanate are usable. Such the fine particles may be used singly or in combination with another kind of additive. It is desirable that these fine particles are subjected to surface treatment by a silane coupling agent, titanium coupling agent, higher fatty acid or silicone oil and the adding amount of the fine particle is from 0.05 to 5 parts by weight, preferably from 0.1 to 3 parts by weight, to 100 parts by weight of the toner.

The electrophotographic toner of the invention can be used as the toner of a two-component developer together with a carrier or an one-component developer without carrier.

As the carrier for two-component developer to be combined with the electrophotographic toner of the invention, for example, a carrier composed of a particle of magnetic substance such as iron and ferrite, a resin coated carrier prepared by coating the magnetic particle with a resin and a binder type carrier prepared by dispersing the fine particles of the magnetic substance into a binder resin are usable.

Among these carriers, a resin coat carrier using a silicone type resin, a copolymer resin (graft resin) of organopolysiloxane and a vinyl type monomer or a polyester type resin is preferably used from the viewpoint of toner spending and a carrier coated with a resin formed by reacting isocyanate to the copolymer resin of organopolysiloxane and a vinyl type monomer is preferable from the viewpoint of durability, environmental stability and ant-spending property. As the above vinyl type monomer, a monomer having a substituent reactive with isocyanate such as a hydroxyl group is necessarily used. The carrier having a volume average diameter of from 20 to 100 μm and preferably from 20 to 60 μm is preferably used for holding high image quality and preventing fog.

(Image Forming Method)

The image forming method include, for example, a method by forming plural images are formed on the photoreceptor and collectively transferred and a method by successively transferring images formed on the photoreceptor onto an intermediate transfer belt. The method by collectively transferring plural images formed on the photoreceptor is more referable.

In such the method, the image formation is carried out as follows. The photoreceptor is uniformly charged and imagewise exposed to light and then firstly developed to form the first toner image on the photoreceptor. Then the photoreceptor having the first image is uniformly charged and imagewise exposed to light corresponding to the second image and secondarily developed to form the second toner image. The photoreceptor having the first and second images is uniformly charged and imagewise exposed to light corresponding to the third image and thirdly developed to form the third toner image. Moreover, the photoreceptor having the first, second and third images is uniformly charged and imagewise exposed to light corresponding to the fourth image and fourthly developed to form the four toner image.

For instance, a full color toner image is formed on the photoreceptor by carrying out the first to fourth developments by each using the yellow, magenta, cyan and black toners, respectively. After that, the image formed on the photoreceptor is collectively transferred onto an image support such as paper and fixed to the image support to obtain the image.

In this method, the images formed on the photoreceptor are collectively transferred onto the paper to form the image. Therefore, the image quality can be raised because the transfer causing disturbance of the image is carried out only at once, different from an intermediate transfer method.

As the developing method, a non-contact development is preferred since plural times of development are necessary. A method in which alternative electric field is applied on the occasion of development is also preferable.

As the above-mentioned, the non-contact developing method is preferable in the system in which a piled color image is formed on the photoreceptor and collectively transferred.

The volume average particle diameter of the carrier is preferably from 15 to 100 μm and more preferably from 25 to 60 μm. The volume average particle diameter of the carrier can be determined by a laser diffraction particle size distribution measuring apparatus having a wet type disperser HELOS manufactured by Sympatec Gmbh.

The carrier is preferably one covered by resin or a resin disperse type carrier in which the magnetic particles are dispersed in the resin. As the resin for coating the carrier, for example, an olefin type resin, a styrene type resin, a styrene/ acryl type resin, a silicone type resin, an ester type resin and a fluorine-containing polymer resin are usable. The resin for preparing the resin disperse type carrier, for example, a styrene/acryl type resin, a polyester resin and a phenol resin are usable.

A heat-contacting method is suitably usable as the fixing method suitably used in the invention. As typical heat-contacting method, a heating roller fixing system and a press and heat fixing system in which fixing is carried out by a rotating roller including a heater can be cited.

(Image)

In the course of image formation by development, transferring and fixing using the electrophotographic toner of the invention, the colored fine particle in the electrophotographic toner is not crushed and the state of dispersed in the toner particle is held even when the toner is transferred onto the image receiving material.

In the invention, the dye is not released or moved on the surface of the toner particle even though the toner particle contains the dye in high concentration by dispersing the colored particles in the toner particle. Therefore, the following problems of the toner prepared by directly dispersing or dissolving the dye into the thermoplastic resin, at the surface of which the dye is exposed, such as that 1) charging amount is low, 2) difference of charging amount at high temperature and high humidity condition and that at low temperature and low humidity condition is large, 3) the charging amount is fluctuated depending on the kind of colorant, for example, the charging amounts of toners respectively using cyan, magenta, yellow and black pigments for full color image recording are different from each other, can be dissolved. Moreover, problems of the dye sublimation and the oil contaminate on the occasion of the fixing by heat are caused on the toner using an usual dye because the moving of the dye as the colorant to outside of the colored fine particle (exposition of the dye onto the surface of the colored fine particle) is not caused on the occasion of the fixing by heating.

EXAMPLES

The invention is described in detail bellow referring examples.

Example 1

Stability Test

To a liquid prepared by dissolving each of 1 g of compounds listed in the Table 1 and comparative compounds 1 and 2 shown below in 30 ml of toluene, each of 20 ml of 0.1N hydrochloric acid (acid test), 20 ml of 0.1N sodium hydrogen carbonate (alkali test) and 20 ml of deionized water (neutral test), were added, and the respective mixture was stirred for 2 days at 60° C. Compounds in toluene phase before and after the test were quantitatively measured by High Performance Liquid Chromatography, and the remaining percentage taking 100% before the test was used as the index of stability.

The result was shown by the following ranking criteria.

A: Residual percentage not less than 95%
B: Residual percentage from 85% to less than 95%
C: Residual percentage from 70% to less than 85%
D: Residual percentage less than 70%

The results are summarized in Table 1.

TABLE 1

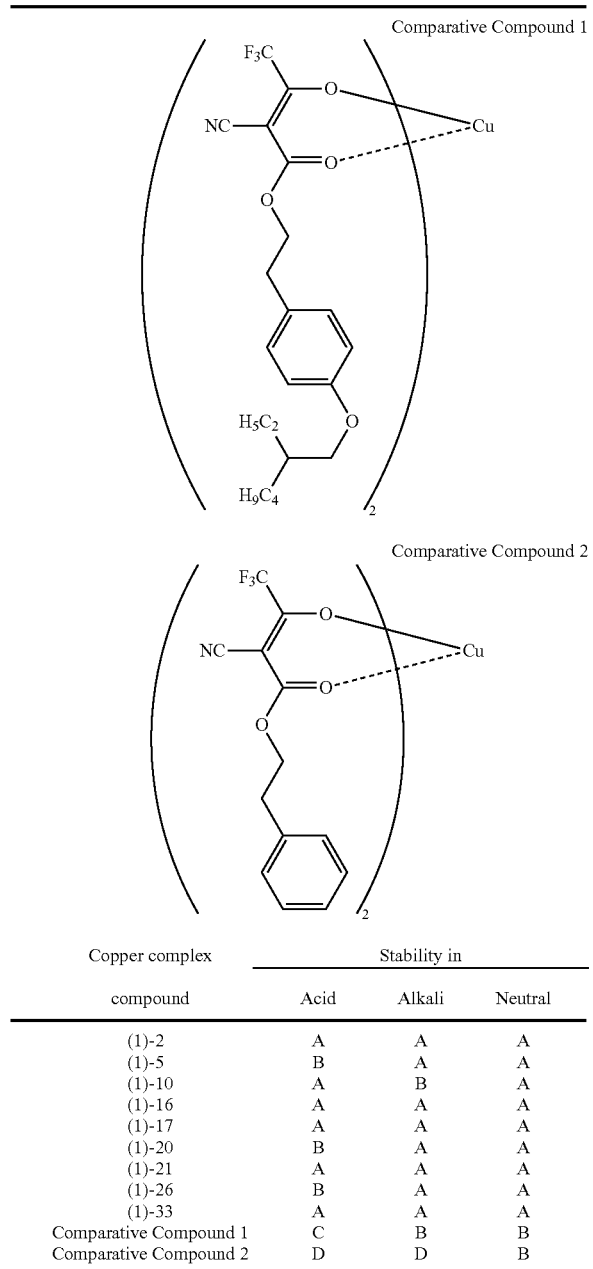

| Copper complex compound | Stability in | | |
|---|---|---|---|
| | Acid | Alkali | Neutral |
| (1)-2 | A | A | A |
| (1)-5 | B | A | A |
| (1)-10 | A | B | A |
| (1)-16 | A | A | A |
| (1)-17 | A | A | A |
| (1)-20 | B | A | A |
| (1)-21 | A | A | A |
| (1)-26 | B | A | A |
| (1)-33 | A | A | A |
| Comparative Compound 1 | C | B | B |
| Comparative Compound 2 | D | D | B |

The result shown in the Table demonstrates that the copper complex compounds according to this invention are excellent in stability regardless liquid properties (acid, alkali or neutral), stable for the use in any condition and advantageous.

Example 2

A pulverized toner and polymerized toner were prepared applying a pulverized toner producing method and two kinds of polymerization toner producing methods.

<Preparation Method of Pulverized Color Toner>

One hundred parts by weight of polyester resin, 2 parts by weight of colorant and the equimolar copper complex compound each shown in Table 1 and 3 parts by weight of propylene resin VISCOL 550P, manufactured by Sanyo Chemical Industries, Ltd., were mixed, kneaded, crushed and classified to obtain a powder having an average particle diameter of 8.5 μm. Then 100 parts by weight of the powder and 1.0 parts of silica fine particles R8.05 having a particle diameter of 12 nm and a hydrophobicity of 60, manufactured by Nippon Aerosil Co., Ltd., was mixed by a Henschel mixer to obtain a crashed toner.

Colorant for yellow toner: Y-1 (shown below), 4 parts
Colorant for magenta toner: Exemplified (2)-1, 2 parts
Colorant for cyan toner: C-1 (shown below), 2 parts

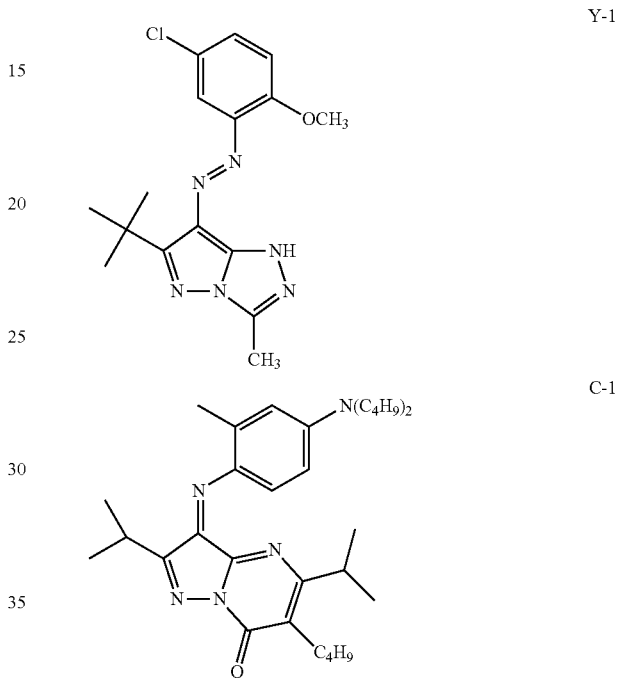

Into a 5,000 ml reaction vessel on which a stirrer, thermal sensor, cooler and nitrogen introduction device were attached, a surfactant solution (aqueous medium) prepared by dissolving 7.08 g of an anionic surfactant $C_{10}H_2(OCH_2CH_2)_2OSO_3Na$ in 3010 g of deionized water was charged and the temperature in the reaction vessel was raised by 80° C. while stirring at 230 rpm under nitrogen atmosphere.

To the surfactant solution, an initiator solution prepared by dissolving 9.2 g of polymerization initiator (potassium persulfate: KPS) in 200 g of deionized water was added and the temperature was adjusted at 75° C., and then a monomer mixture composed of 70.1 g of styrene, 19.9 g of n-butyl methacrylate, 10.9 g of methacrylic acid and 10 g of t-dodecylmercaptane was dropped spending 1 hour. The system was heated and stirred at 80° C. for 2 hours for performing polymerization (the first step polymerization) to prepare a latex (a dispersion of resin particles composed of a high molecular weight resin).

In a flask on which a stirrer was attached, a monomer solution was prepared by adding 98.0 g of a crystallizable substance WEP-5, manufactured by NOF Corp., to a monomer mixture composed of 105.6 g of styrene, 30.0 g of n-butyl acrylate, 6.2 g of methacrylic acid and 5.6 g of t-dodecylmercaptane. Besides, a surfactant solution prepared by dissolving 1.6 g of the foregoing anionic surfactant in 2,700 ml of deionized water was heated by 82° C. and 28 g in terms of solid component of the foregoing latex as the dispersion of core particles was added to the surfactant solution. And then the monomer liquid containing WEP-5 was mixed and dispersed in the above dispersion spending 0.5 hours by a mechanical dispersing machine having a circulation pass CLEARMIX, manufactured by M-Tec Co., Ltd., to prepare a dispersion (emulsion) containing emulsified particles (oil droplets). After that, an initiator solution prepared by dissolving 5.1 g of the polymerization initiator (KPS) in 240 ml of deionized water and 750 ml of deionized water were added to the above dispersion (emulsion) and the resultant system was heated and stirred at 82° C. for 12 hours to carry out polymerization (the second step polymerization. Thus a latex (a dispersion of fine resin particles structured by a high molecular resin covered with medium molecular weight resin on the surface thereof) was obtained. The latex was referred to as Latex 1.

(Preparation of Colorant Dispersion)

| Colorant | 50 parts by weight |
|---|---|
| Copper complex compound | Equimolar of the colorant |
| Sodium dodecylsulfate | 10 parts by weight |
| Deionized water | 200 parts by weight |

The above composition was dispersed by a sand grinder to obtain a colorant fine particle dispersion having a volume average particle diameter (D50) of 100 nm.

(Preparation of Toner Particle)
Formation of Core Particle 1

Into a reaction vessel (a four-mouth flask) on which a thermal sensor, cooler, nitrogen introducing device and stirrer, 420.7 g in terms of solid component of Latex 1, 900 g of deionized water and 1166 g of the colorant dispersion were charged and stirred. After adjusting the temperature in the vessel at 30° C., pH of the resultant dispersion was controlled to within the range of from 8 to 10 by adding a 5N sodium hydroxide aqueous solution. Then an aqueous solution prepared by dissolving 12.1 g of magnesium chloride hexahydrate in 1,000 ml of deionized water was added to the above dispersion spending 10 minutes at 30° C. After stirring for 10 minutes, the dispersion was heated by 80° C. to form fused particles spending 90 minutes for growing particle diameter.

In the above situation, the diameter of the fused particle was measured by Coulter Counter TA-II and an amount corresponding to 15% of the total amount in terms of solid component of the core latex (core particles) of polyester-containing resin slurry A (shell particles) was added and dispersed together with an aqueous solution of 3 g of the surfactant in 1,000 ml deionized water at the time when the number average particle diameter is reached at 6.1 μm Then the above system was stirred for 4 hours while dropping an aqueous solution prepared by dissolving 15 g of the coagulation agent (magnesium chloride hexahydrate) in 1,000 ml of deionized water. After that, an aqueous solution prepared by dissolving 80.4 g of sodium chloride in 1,000 ml of deionized water was added for stopping the particle growing and the system was subjected to ripening by heating and stirring at 95° C. for 2 hours or continuing the fusion of particles phase separation of crystallizable substance (ripening process). After that, the system was cooled by 30° C. and the pH was adjusted to 2.0 and then stirring was stopped. The resultant fused particles were filtered and repeatedly washed by deionized water of 45° C. and then dried by air warmed at 40° C. Thus toner particles were obtained.

The obtained toner particles and 1.0 part of the foregoing silica fine particles R805 were mixed by a Henschel mixer to obtain Polymerization Toner 1.

(Preparation of Toner Particle 2)
Formation of Core Particle 2

Into a reacting vessel (four-mouth flask) on which a thermal sensor, cooler, nitrogen introducing device and stirrer were attached, 420.7 g in terms of solid component of Latex 1, 900 g of deionized water and 1166 g of the colorant dispersion were charged and stirred. The temperature in the vessel was adjusted to 30° C. and an aqueous solution prepared by dissolving 12.1 g of magnesium chloride hexahydrate in 1,000 ml of deionized water was added spending 10 minutes at 30° C. while stirring, the pH of the dispersion on this occasion was 5 to 6. After standing for 10 minutes, the temperature was raised by 84° C. and fused particles were formed (particle diameter growing time was 90 minutes).

The operation after the above was the same as in the preparation of Toner 1. Thus Polymerized Toner 2 was obtained.

{Development and Evaluation}

Each of the Developers 1 through 24 obtained as above was subjected to practical image forming test on paper and OHP sheet under ordinary temperature and humidity condition (at 25° C. and a relative humidity of 55%) using a digital copying machine KONICA 7075, manufactured by KONICA Corp., modified as follows and evaluated as to (1) color reproducibility, (2) transparence, (3) Fastness against light. and (4) resistivity against heat and humidity. Developing conditions were as follows.

(Developing Conditions)
Surface potential of photoreceptor: −700 volt
DC bias: −500 V
Distance between photoreceptor and developing sleeve Dsd: 600 μm
Developer layer regulation: Magnetic H-Cut system
Developer layer thickness: 700 μm
Developing sleeve diameter: 40 mm (Fixing Device)

A heating roller type fixing device was used. Concretely, a heating roller was constituted by coating the surface of a cylindrical metal core (inner diameter: 40 mm, wall thickness: 1.0 mm, entire width: 310 mm) including a heater at the center portion thereof and covered by a layer of tetrafluoroethylene perfluoroalkylvinylether copolymer (PFA) having a thickness of 120 μm and a pressing roller constituted by covering a cylindrical metal core (inner diameter: 40 mm, wall thickness: 2.0 mm) by silicone rubber sponge were contacted with each other by a pressure of 150 N to form a nip of 5.8 mm width. The line speed of printing was set at 480 mm/sec using the above fixing device. For cleaning the fixing device, a supplying system using a web impregnated with polyphenylsilicone having a viscosity of 10 Pa·s at 20° C. was used. The fixing temperature was controlled according to the surface temperature of the heating roller set at 175° C. The coating amount of the silicone oil was 0.1 mg/A4.

(Color Reproducibility)

The color reproducibility of a mono-color image formed on copy paper was visually evaluated by 10 monitors according to the following norms. The evaluation was carried out within the adhering amount of the toner of $0.7\pm0.05$ mg/cm$^2$. Evaluation results are shown in Table 1.

A: The reproducibility was particularly excellent (clear color).
B: The reproducibility was excellent.
C: Some degree of color contamination was observed (color with some contamination)
D: Problem on the image quality was caused by color contamination (bluish or turbid bluish color was felt).

(2) Transparency

A transparent image (OHP image) was formed for evaluating the transparency of image. The visible light spectral transmittance of the fixed image was measured by 330 type automatic spectral photometer, manufactured by Hitachi Ltd., referring the transmittance of the OHP sheet on which no toner was carried. The difference of the transmittance measured at 650 nm and that at 450 nm as to yellow toner, the difference of that at 650 nm and that at 550 nm as to the magenta toner and the difference that at 500 nm and that at 600 nm as to cyan toner were determined and evaluated according to the following norms. When such the value is not less than 70%, the transparency is judged as good. The evaluation was carried out within the adhering amount of the toner of $0.7\pm0.05$ mg/cm$^2$.

A: Not less than 90%
B: Eighty percent to less than 90%

(4) Heat and Humidity Fastness

The heat and humidity fastness was evaluated by measuring the image density Ci just after recording and measuring again the image density Cf after storage for 14 days under conditions of 50° C. and 80% RH. The dye remaining ratio $\{(Ci-Cf)/Ci\times100\%\}$ was calculated from the difference of the densities each measured before and after the storage. The image density was measured by a reflective densitometer X-Rite 310TR. The change in the color was visually observed. The evaluation results are shown in Table 12.

AA: The dye remaining ratio was not less than 95%.
A: The dye remaining ratio was 90% to 95%.
B: The dye remaining ratio was 80% to less than 90%.
C: The dye remaining was less than 80% and a little contamination in color was visually observed.
D: The dye remaining was less than 80% and contamination in color was visually observed.

TABLE 2

| Developer | Copper complex compound | Colorant | Color reproducibility | Transparency | Light fastness | Heat and humidity fastness | Preparation method |
|---|---|---|---|---|---|---|---|
| 1 | None | Y-1 | B | A | C | C | *** |
| 2 | None | (2)-1 | C | A | C | C | *** |
| 3 | None | C-1 | C | A | C | C | *** |
| 4 | (1)-16 | Y-1 | A | A | A | A | *** |
| 5 | (1)-16 | (2)-1 | A | A | A | A | *** |
| 6 | Comp 1 * | (2)-1 | A | A | B | C | *** |
| 7 | (1)-16 | C-1 | A | A | A | A | *** |
| 8 | (1)-16 | (2)-23 | B | A | A | A | 1 # |
| 9 | (1)-16 | (2)-27 | A | A | A | A | 1 # |
| 10 | Comp 1 * | (2)-23 | B | A | B | C | 1 # |
| 11 | (1)-4 | (2)-7 | A | A | A | A | 2 ## |
| 12 | (1)-7 | (2)-9 | A | A | A | B | 2 ## |
| 13 | (1)-17 | (2)-10 | A | A | A | A | 2 ## |
| 14 | (1)-18 | (2)-12 | A | A | A | A | 2 ## |
| 15 | (1)-20 | (2)-15 | A | A | A | B | 2 ## |
| 16 | (1)-21 | (2)-16 | A | A | A | A | 2 ## |
| 17 | (1)-27 | (2)-18 | A | A | B | A | 2 ## |
| 18 | (1)-32 | (2)-19 | B | A | A | A | 2 ## |
| 19 | (1)-36 | (2)-25 | A | A | B | A | 2 ## |
| 20 | (1)-40 | (2)-30 | B | A | A | A | 2 ## |
| 21 | (1)-17 | (2)-10 | A | A | AA | AA | 2 ## |
| 22 | (1)-17 | (2)-10 | A | A | B | A | 2 ## |
| 23 | Comp 1 * | (2)-10 | B | B | C | C | 2 ## |
| 24 | Comp 1 * | (2)-10 | C | B | D | D | P2 ## |
| 25 | Comp 2 ** | (2)-10 | B | B | D | D | 2 ## |

Comp A *: Comparative Dye A,
Comp B **: Comparative Dye B,
Comp 1 *: Comparative Compound 1,
Comp 2 *: Comparative Compound 2,
*** Pulverization method
1 #: Polymerization method 1
2 ##: Polymerization method 2

C: Seventy percent to less than 80%
D: Less than 70%

(3) Light Fastness

The image density just after recording Ci was measured and then the image density Cf was measured again after exposed to 70,000 lux of xenon light for 14 days by a weathermeter Atlas C 165. The dye remaining ratio $\{(Ci-Cf)/Ci\times100\%\}$ was calculated from the difference of the densities each measured before and after the light exposure. The image density was measured by a Reflective densitometer X-Rite 310TR. The evaluation results are shown in Table 1.

AA: The dye remaining ratio was not less than 98%.
A: The dye remaining ratio was 95% to 98%.
B: The dye remaining ratio was 90% to less than 95%.
C: The dye remaining ratio was 80 to less than 90%.
D: The dye remaining ratio was less than 80%.

In Developer 20, the copper complex compound was added in an amount of 2 times in mole of the colorant. In Developer 21, the copper complex compound was added in an amount of 0.8 times in mole of the colorant. In the other developers, the adding amount of the copper complex compound was equimolar with the colorant in mole.

It is understood from the results shown in Table 1 that the toner excellent in the light fastness and the resistivity against heat and humidity can be obtained by using the colorant and copper compound of the invention regardless of the production method.

Moreover, it is found that the polymerization toner is also excellent in the light fastness and the resistivity against heat and humidity regardless of the production method. Furthermore, it is understood that the light fastness is further raised by increasing the amount of the copper complex compound and the effect of it was held in some degree even when the adding amount is reduced.

The invention claimed is:

1. A copper complex compound represented by Formula (1),

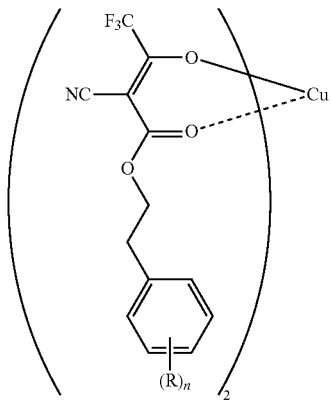

Formula (1)

wherein R comprises an alkyl group, an alkoxyl group, a sulfamoyl group, or a carbamoyl group, wherein each of the sulfamoyl group and the carbamoyl group further comprises a substituent containing carbon atoms, n is an integer of from 1 to 5 and the total number of carbon atoms contained in (R)n is 14 or more.

2. The copper complex compound of claim 1, wherein logP of one molecule of the ligand is not less than 9.

3. The copper complex compound of claim 1, wherein R further comprises an aryl group, a heterocyclic group, a heteroaryl group, an ureido group, an amino group, an amido group, an acyl group, an alkoxycarbonyl group, a a cyano group or a halogen atom.

4. The copper complex compound of claim 1, wherein R is an alkoxy group.

5. The copper complex compound of claim wherein n is 1 in the Formula (1).

* * * * *